United States Patent
Sarkis et al.

(10) Patent No.: US 7,018,628 B1
(45) Date of Patent: Mar. 28, 2006

(54) VECTORS DERIVED FROM BACULOVIRUS AND USE FOR TRANSFERRING NUCLEIC ACIDS INTO NERVE CELLS OF VERTEBRATES

(75) Inventors: Chamsy Sarkis, Paris (FR); Jacques Mallet, Paris (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 09/744,488

(22) PCT Filed: Jul. 23, 1999

(86) PCT No.: PCT/FR99/01813

§ 371 (c)(1),
(2), (4) Date: May 11, 2001

(87) PCT Pub. No.: WO00/05394

PCT Pub. Date: Feb. 3, 2000

Related U.S. Application Data

(60) Provisional application No. 60/122,792, filed on Mar. 4, 1999.

(30) Foreign Application Priority Data

Jul. 24, 1998 (FR) .................................. 98 09457

(51) Int. Cl.
*A61K 48/00* (2006.01)
*C12N 15/866* (2006.01)
(52) U.S. Cl. .................................. 424/93.2; 435/320.1
(58) Field of Classification Search ................ 435/456, 435/320.1, 69.1, 69.4, 69.52, 69.8, 70.3; 424/93.2
See application file for complete search history.

(56) References Cited

FOREIGN PATENT DOCUMENTS

| WO | WO 98/11243 A | | 3/1998 |
|----|---------------|---|--------|
| WO | WO9812311 | * | 3/1998 |

OTHER PUBLICATIONS

Verma et al., Nature, vol. 389, pp. 239-242 (1997).*
Palu et al., J. Biotechnol. vol. 68:1-13 (1999).*
Fox, ASM News, Feb. vol. 66 (2), pp. 1-3 (2000).*
Li et al., Biochem. J., vol. 324 pp. 461-466 (1997).*
Kelly, Experimental Neurology, 144, 157-159, 1997.*
Brooks et al., J. Neuroscience Methods, 80, 137-147, 1998.*
Boyce, F.M. et al., Baculovirus-mediated Gene Transfer Into Mammalian Cells, PNAS 93:2348-2352 (Mar. 1996).
Shoji, I. et al., Efficient Transfer into Various Mammalian Cells, including Non-Hepatic Cells, By Baculovirus Vectors, Journal of General Virology, 78(10):2657-2664 (1997).
Hofmann, C. et al., Efficient Gene Transfer Into Human Hepatocytes by Baculovirus Vectors, PNAS USA 92:10099-10103 (1995).
Sandig, V. et al., Gene Transfer into Hepatocytes and Human Liver Tissue by Baculovirus Vectors, Human Gene Therapy, 7:1937-1945 (1996).
Barsoum, J. et al., Efficient Transduction of Mammalian Cells bya Recombinant Baculovirus Having the Vesicular Stomatitis Virus G. Glycoprotein, Human Gene Therapy, 8:2011-2018 (1997).

* cited by examiner

*Primary Examiner*—Nancy Vogel
(74) *Attorney, Agent, or Firm*—Nixon & Vanderhye P.C.

(57) ABSTRACT

The invention concerns novel recombinant viruses and their use for gene-transfer into nerve cells of vertebrates. The invention also concerns pharmaceutical compositions comprising said recombinant viruses. More particularly, the invention concerns novel vectors derived from baculoviruses and their use for treating diseases of the nervous system of vertebrates.

6 Claims, 8 Drawing Sheets

Figure 1:
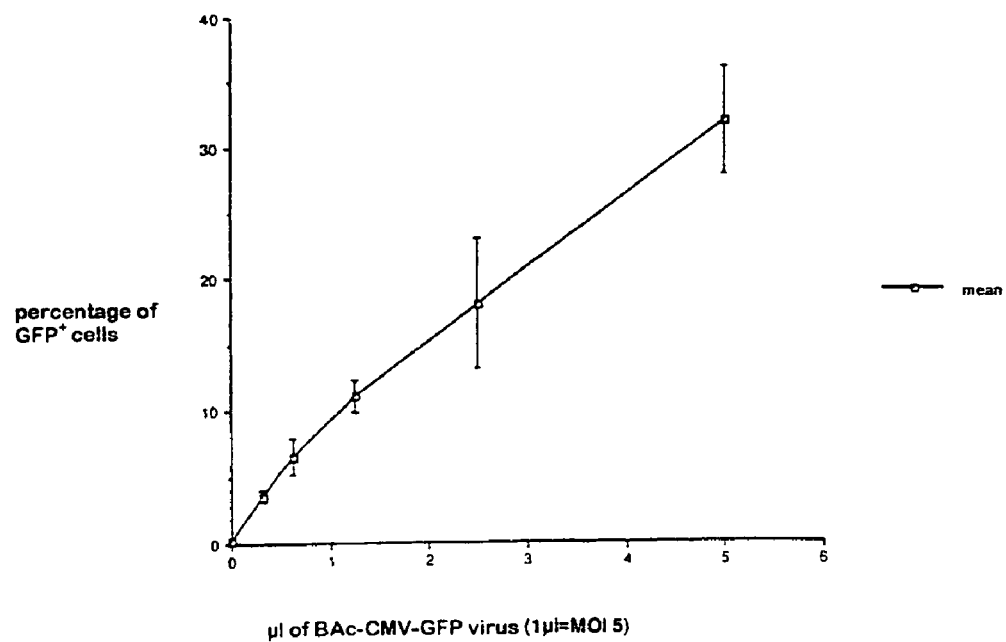

VECTORS DERIVED FROM BACULOVIRUS AND USE FOR TRANSFERRING NUCLEIC ACIDS INTO NERVE CELLS OF VERTEBRATES

PRIORITY CLAIM

This application is a 35 U.S.C. § 371 filing of PCT Application number PCT/FR99/01813 filed on Jul. 23, 1999, which claims the benefit of French Application number FR98/09457 filed on Jul. 24, 1998 and U.S. Provisional Application No. 60/122,792, filed Mar. 4, 1999.

The invention relates to new recombinant viruses and their use for the transfer of genes into the cells of the nervous system of vertebrates. It also relates to the pharmaceutical compositions comprising said recombinant viruses. More particularly, the present invention relates to new factors derived from baculoviruses and their use for the treatment of diseases of the nervous system of vertebrates.

Baculoviruses are circular double-stranded DNA-containing enveloped viruses which are specific to invertebrates. Their prototype, AcNPV (*autographa californica* multiple nuclear polyhedrosis virus), has a genome of 133 kb. This vector is very widely used as eukaryotic gene expression vector in insect cells, using two strong promoters [polyhedrin (Ph) and P10], (King and Possee, The baculovirus expression system. London: Chapman & Hall, 1992.).

Baculovirus stocks may be prepared by infecting insect cells (Sf9 or Sf21) with the recombinant baculovirus. The production of protein occurs by infecting insect cells with the baculovirus: the cellular medium is harvested and the protein synthesized in vitro in the insect cells is extracted.

Recombinant baculoviruses are obtained by homologous recombination in insect cells (generally Sf9 or Sf21) between the shuttle plasmid containing the transgene under the control of an active promoter in the cells of vertebrates and the baculovirus genome linearized at the level of the recombination site, or by other techniques well known to persons skilled in the art (transposons, recombination in yeast and the like). Baculoviruses are episomal viruses (in the insect), and make it possible to integrate therein up to 100 kb of recombinant DNA. Thus they have many advantages linked to their ease of production (multiplication in insect cells, industrializable culture conditions, production of high titers), to their large cloning capacity, and to the fact that they exhibit a low risk of dissemination because they are neither replicative in mammals nor disseminative in insects. These vectors have nevertheless not been used in the field of gene therapy because, on the one hand and until very recently, it was accepted that these viruses did not infect mammalian cells, and, on the other hand, the transfection of baculoviruses in vivo in mammals has never yet been demonstrated.

Hoffmann et al. (PNAS USA 92 (1995) 10099–10103) have shown that a recombinant baculovirus containing a reporter gene under the control of the CMV early promoter is capable of infecting and of expressing the transgene in hepatocytes with a very good efficiency: humans (primary culture, Huh7 and HepG2 line) and murines (rabbit primary culture). However, these others did not observe a significant expression of the transgene in a whole series of lines of various origins, including the nervous system (mouse neuroblastoma Neuro-2a, human astrocytoma SW1088 and rat pheochromocytoma PC12).

Boyce F. M. and Bucher N. L. R. PNAS USA 93 2348–2352 (1996) have obtained a significant expression of the LacZ gene placed under the control of an RSV promoter in the HepG2 line as well as in the lines 293 (human kidney) A549 (human lung) and PC12 (rat pheochromocytoma). They did not obtain a significant expression in all the other lines tested.

Sandig V. et al. (Human Gene therapy 7 1937–1945 (1996) have used a recombinant baculovirus RSV-LacZ for the infection of human and murine hepatocytes. They have shown that the virus is sensitive to complement and cannot therefore infect the liver in vivo. They have nevertheless obtained infection of a piece of human liver infused ex vivo with the baculovirus, after removal of the serum.

More recently, Shoji et al. (J. Gen. Virol. 1997) have used a recombinant baculovirus containing a reporter gene under the control of the CAG promoter (CMV early enhancer and the chicken β-actin promoter), and have obtained a significant expression in various cell lines (HepG2, Huh7, CPK, Cos7, Hela, FS-L3 KATO- III). A low expression was detected in the lines RGM-1, PC12, IMR-32 and MT-2.

Barsoum et al (Human Gene Therapy, 8 2011–2018 (1997)) have shown that it was possible to modify the viral envelope of a baculovirus containing a β-galactosidase expression cassette under the control of the RSV LTR. This makes it possible to enhance the transduction potential of these vectors, while enhancing the infection of cells infectable with the baculovirus whose envelope is not modified. This also makes it possible to infect cells which were not infectable with the baculovirus whose envelope was not modified. However, the authors did not test the infection of nerve cells. Furthermore, they did not succeed in transducing the Neuro2a (or N2a) cells which are derived from a mouse neuroblastoma.

Thus, up until now, no baculovirus vector has been used for the transfer of genes in vitro or in vivo into the cells of the nerve tissue. Indeed, only the PC12 line, which is capable of exhibiting a "pseudoneuronal" phenotype (rat phechromocytoma: peripheral nervous system) under specific conditions, has been found to be capable of being infected by the baculovirus; however, the level of expression remained very slightly higher than that of the control. Finally, no use of the baculovirus for gene transfer in vivo in mammals has been described up until now.

The applicant has now shown that it is possible to construct recombinant baculoviruses comprising a heterologous nucleic acid sequence preferably encoding a product of therapeutic interest for the treatment of diseases of the nervous system, to administer these recombinant baculoviruses in vivo, and that this administration allows a stable and localized expression of the transgene in vivo, and in particular in the nervous system. Indeed, the results presented in the examples demonstrate that the baculoviruses of the invention can infect and direct the expression of transgene in the cells of the nervous system of vertebrates and preferably of humans. By way of illustration of the invention, the examples of the present application surprisingly report the expression of a transgene of interest in at least 60% of differentiated cells of a primary culture of human telencephalon and/or an expression in at least 30% of progenitor telencephalic cells as well as 30% of astrocytes of a primary culture of an adult human cortex. The present invention thus provides viral vectors which can be used directly in gene therapy, which are particularly suitable and effective for directing the expression of transgenes of therapeutic interest in vivo in the nervous system or for an application ex vivo for the transfer of genes in cultures of cells of the nervous system and the like (Sertoli cells, muscle cells, and the like) which are intended to be transplanted. The present invention thus offers a particularly advantageous new approach for the treatment and/or prevention of neurodegenerative diseases or for the treatment of metabolic diseases requiring a specific treatment of the nervous system because of the poor accessibility of therapeutic agents which do not cross the blood-brain barrier.

A first subject of the invention consists in recombinant baculoviruses comprising a heterologous nucleic acid sequence encoding a product of therapeutic interest for the treatment of diseases of the nervous system.

In particular, the heterologous nucleic acid sequence may contain one or more therapeutic genes.

The therapeutic genes which can thus be transferred are any gene whose transcription and, possibly, translation in the target cell generate products having a therapeutic effect.

The protein product thus encoded may be a protein or a peptide. This protein product may be homologous with respect to the target cell (that is to say a product which is normally expressed in the target cell when it has no pathological condition). In this case, the expression of a protein makes it possible, for example, to compensate for an insufficient expression in the cell or the expression of an inactive or weakly active protein because of a modification, or alternatively to overexpress said protein. The therapeutic gene may also encode a mutant of a cellular protein having increased stability, a modified activity, and the like. The protein product may also be heterologous with respect to the target cell. In this case, an expressed protein may, for example, complement or provide an activity which is deficient in the cell, allowing it to combat a pathological condition, or alternatively to inhibit the expression of a protein in the cells, by the use of negative mutants for example.

Among the therapeutic product for the purposes of the present invention, there may be mentioned more particularly hormones, lymphokines: interleukins, interferons, TNF, and the like (FR 9203120), growth factors, enzymes for synthesizing neurotransmitters, trophic factors, in particular neurotrophic factors for the treatment of neurodegenerative diseases, traumas which have damaged the nervous system, or retinal degeneration. For example, members of the neurotrophin family such as NGF, BDNF, NT3, NT4/5, NT6 and their derivatives, members of the CNTF family such as CNTF, axokine, LIF and their derivatives, IL6, cardiotrophin, GDNF and its derivatives, members of the IGF family such as IGF-1 and IFGF-2, members of the FGF family such as FGF 1, 2, 3, 4, 5, 6, 7, 8 and 9, and their derivatives, and TGF-β.

Among the therapeutic products for the purposes of the present invention, there may also be mentioned tumor suppressor genes: p53, Rb, Rap1A, DCC, k-rev and the like (FR 93 04745), suicide genes: thymidine kinase, cytosine deaminase, and the like.

The nucleic acid sequences encoding products of therapeutic interest for the purposes of the present invention also cover the genes encoding the proteins involved in the metabolism of amino acids, lipids and other constituents of the cell.

There may thus be mentioned, with no limitation being implied, the genes associated with carbohydrate metabolism diseases such as for example fructose-1-phosphate aldolase, fructose-1,6-diphosphatase, glucose-6-phosphatase, lysosomal α-1,4-glucosidase, amylo-1,6-glucosidase, amylo-(1,4: 1,6)-transglucosidase, muscular phosphorylase, muscular phosphofructokinase, phosphorylase-b-kinase, galactose-1-phosphate uridyl transferase, all the enzymes of the pyruvate dehydrogenase complex, pyruvate carboxylase, 2-oxoglutarate glyoxylase carboxylase, D-glycerate dehydrogenase.

There may also be mentioned:

the genes associated with amino acid metabolism diseases such as for example phenylalanine hydroxylase, dihydrobiopterin synthetase, tyrosine aminotransferase, tyrosinase, histidinase, fumarylacetoacetase, glutathione synthetase, γ-glutamylcysteine synthetase, ornithine-5-aminotransferase, carbamoylphosphate synthetase, ornithine carbamoyltransferase, argininosuccinate synthetase, argininosuccinate lyase, arginase, L-lysine dehydrogenase, L-lysine ketoglutarate reductase, valine transaminase, leucine isoleucine transaminase, branched chain 2-keto acid decarboxylase, isovaleryl-CoA dehydrogenase, acyl-CoA dehydrogenase, 3-hydroxy-3-methylglutaryl-CoA lyase, acetoacetyl-CoA 3-ketothiolase, propionyl-CoA carboxylase, methylmalonyl-CoA mutase, ATP:cobalamin adenosyltransferase, dihydrofolate reductase, methylene tetrahydrofolate reductase, cystathionine β-synthetase, sarcosine dehydrogenase complex, proteins belonging to the glycine cleavage system, β-alanine transaminase, serum carnosinase, cerebral homocarnosinase.

The genes associated with fat and fatty acid metabolism diseases such as, for example, lipoprotein lipase, apolipoprotein C-II, apolipoprotein E, other apolipoproteins, lecithin-cholesterol acyltransferase, LDL receptor, liver sterol hydroxylase, "phytanic acid" α-hydroxylase.

The genes associated with lysosomal deficiencies such as, for example, lysosomal α-L-iduronidase, lysosomal iduronate sulfatase, lysosomal heparan N-sulfatase, lysosomal N-acetyl-α-D-glucosaminidase, lysosomal acetyl-CoA:α-glucosamine N-acetyltransferase, lysosomal N-acetyl-α-D-glucosamine 6-sulfatase, lysosomal galactosamine 6-sulfate sulfatase, lysosomal β-galactosidase, lysosomal arylsulfatase B, lysosomal β-glucuronidase, N-acetylglucosaminylphosphotransferase, lysosomal α-D-mannosidase, lysosomal α-neuramimidase, lysosomal aspartylglycosaminidase, lysosomal α-L-fucosidase, lysosomal acid lipase, lysosomal acid ceramidase, lysosomal sphingomyelinase, lysosomal glucocerebrosidase and lysosomal galactocerebrosidase, lysosomal galactosylceramidase, lysosomal arylsulfatase A, α-galactosidase A, lysosomal acid β-galactosidase, lysosomal hexosaminidase A α chain.

There may also be mentioned, without any restriction, the genes associated with steroid and lipid metabolism diseases, the genes associated with purine and pyrimidine metabolism diseases as well as the genes associated with porphyrin and heme metabolism diseases.

The heterologous nucleic acid sequence may be an antisense sequence or gene whose expression in the target cell makes it possible to control the expression of genes or the transcription of cellular mRNA. Such sequences may for example be transcribed, in the target cell, into RNAs complementary to cellular mRNAs and may thus block their translation into protein, according to the technique described in patent EP 140 308, into autocatalytic RNAs such as ribozymes as well as into RNA modifying splicing in trans.

Generally, the heterologous nucleic acid sequence also comprises a promoter region for transcription which is functional in the infected cell. It may be a promoter region which is naturally responsible for the expression of the gene considered when it is capable of functioning in the infected cell. It may also be regions of a different origin (which are responsible for the expression of other proteins, or which are even synthetic). In particular, it may involve promoter sequences of eukaryotic or viral genes. For example, it may involve promoter sequences derived from the genome of the cell which it is desired to infect. Advantageously, it is a promoter which is active in nerve cells or tissues, especially a eukaryotic promoter. In this regard, it may be for example a ubiquitous promoter, that is to say which is functional in the majority of cell types. Still more preferably, it may therefore be a eukaryotic ubiquitous promoter. The promoter may be autologous, that is to say derived from the same species as the cell in which the expression is sought, or xenogeneic (obtained from another species). There may be mentioned by way of advantageous examples eukaryotic ubiquitous promoters, strong promoters such as the promoter of the phosphoglycerate kinase 1 (PGK) gene or other promoters directing the expression of the genes for obligatory cellular metabolism (these genes are termed housekeeping genes and specify proteins necessary for functions common to all cells). They are for example genes involved in the Krebs cycle, in cellular respiration or in the replication or transcription or the translation (EF 1-α). There may be mentioned as specific examples of this type of promoters the promoter of the α1-antitrypsin, β-actin, vimentin aldolase A or Eflα (elongation factor) genes.

The promoter used in the context of the invention may also be a eukaryotic promoter specific to nerve cells. There may be mentioned by way of example the promoter of the NSE (Neuron Specific Enolase), NF (Neurofilament), TH (Tyrosine Hydroxylase), DAT (Dopamine Transporter), ChAT (Choline Acetyl Transferase), DBH (Dopamine β-Hydroxylase, TPH (Tryptophan Hydroxylase), GAD (Glutamic Acid Dehydrogenase) and GFAP (Glial Fibrillary Acidic Protein) genes and, more generally, all the promoters of synthesis enzymes or of transporters of neuromediators or any other promoter of genes whose expression is specific to a given neuronal or glial type or subtype.

It is also possible to envisage the use of viral promoters such as, for example, the CMV (Cytomegalovirus), RSV (Rous Sarcoma Virus), TK (Thymidine Kinase), SV40 (Simian Virus) and RSV, MLV (Murine Leukemia Virus) or HIV (Human Immunodeficiency Virus) LTR (Long Terminal Repeat) promoters.

It is also possible to envisage using chimeric promoters such as CAG (CMV enhancer and chicken β-actin promoter), NRSE-PGK or inducible promoters such as the promoters inducible by tEtracycline (Tet-On and Tet-Off), the promoters inducible with ecdysone or alternatively other inducible promoters (RU486, 17β-Estradiol and the like) and in particular promoters inducible by stress, such as heat stress (hsp 70).

In addition, these promoter regions can be modified by addition of activating sequences, regulatory sequences or sequences allowing a tissue-specific or predominant expression.

Moreover, the heterologous nucleic acid sequence may also contain a signal sequence directing the therapeutic product synthesized in the secretory pathways of the target cell or in a specific compartment of the cell. This signal sequence may be the natural signal sequence of the therapeutic product, but it may also be any other functional signal sequence or an artificial signal sequence.

The virus may be used both in an ex vivo and in vivo approach. In the context of a gene therapy applicable to humans, it is possible to envisage an ex vivo approach by transplanting cells modified genetically by a recombinant baculovirus. These cells may be of various origins: nervous origins (human or non human), Sertoli cells, chromaffine cells and the like. The combination of certain medicaments may be envisaged with a view in particular to improving the retention of the transplant or the expression of the transgene (immunosuppressants, anti-complement and the like). It is also possible to envisage the implantation of cells genetically modified by a recombinant baculovirus after encapsidation in an inert system.

The baculoviruses according to the invention can be prepared by any techique known to the person skilled in the art. In particular, they can be prepared by homologous recombination between a shuttle plasmid and the genome of *Autographa california* in Sf9 cells and amplified in these same cells according to the method described by Gruenwald S. and Heitz J., 1993 (Baculovirus expression vector system, procedure & method manual. Pharmingen Eds, San Diego, Calif.). Next, the baculoviruses which have multiplied are recovered and purified according to conventional molecular biology techniques as illustrated in the examples.

The baculoviruses of the invention cover any derivative of a baculovirus as described and produced above. The expression derivative should be understood to mean any baculovirus having its genome modified either by insertion of sequences into or by deletion of viral genes from the said genome. In particular, the baculovirus derivatives are obtained by deletion of all or part of one or more viral genes. By way of example, there may be mentioned the deletion of the polyhedrin gene, of the P10 gene as well as of any gene which is not essential for the replication of the baculovirus in insect cells in particular. A particular derivative is represented by the deletion of all the baculovirus viral genes (gutless virus) allowing the insertion of a large-size expression cassette.

It is also possible to modify the envelope of the baculoviruses, that is to say to cause an envelope protein other than those of baculoviruses to be expressed at their surface, thus making it possible to modify the host range of the virus. It is thus possible to use envelopes which make it possible to broaden the host range to a very wide variety of cell types or it is possible on the contrary to envisage restricting the host range to a specific type of nerve cell. Among the envelope proteins which can be used, there may be mentioned in particular: the glycoprotEin of VSV, the amphotropic envelope protein of MLV. It is also possible to use envelope proteins which make it possible to specifically enhance the entry of the virus into neural cells (CNS and/or PNS) such as the rhabdovirus and in particular the rabies virus glycoprotein, the togavirus envelope glycoprotein (alphavirus including Semliki Forest and Sindbis virus, and rubivirus) and in particular the rubella (rubivirus) envelope glycoprotein, the Herpesvirus (HSV) glycoprotein, or any other neurotropic virus. Preferred variants of recombinant baculoviruses according to the invention are baculoviruses pseudotyped with the glycoprotein of the rabies virus or the glycoprotein of VSV (Vesicular Stomatitis Virus).

These recombinant vectors can be used for the transfer of nucleic acids into the cells of the nervous tissues in vitro, ex vivo or in vivo.

The application in vivo may be made especially by stereotaxic injection of the recombinant baculovirus into the central nervous system (brain, medulla) and in particular in the parenchyma or into the spaces containing the cerebrospinal fluid (intraventricular or intrathecal for example). In this regard, it is possible to use the combination of complement inhibitors (CVF, sCR1 (Hoffman et al., Gene Therapy, 1998, vol. 5, pp. 531–536), FUT175 and the like) to enhance the transfection efficiency. It is also possible to envisage carrying out the administration of the baculovirus, especially into muscle, so as to reach the nervous system by reverse transport of the baculovirus and/or of the therapeutic product. In the latter case, the injection will be advantageously preceded by inhibition of the complement system in vivo.

As indicated above, the present invention also relates to any use of a baculovirus as described above for the preparation of a pharmaceutical composition intended for the treatment and/or prevention of diseases of the nervous system. More particularly, it relates to any use of these baculoviruses for the preparation of a pharmaceutical composition intended for the treatment and/or prevention of Parkinson's disease, Alzheimer's disease, amyotrophic lateral sclerosis (ALS), Huntington's disease, epilepsy, multiple sclerosis or other diseases affecting myelinization, as well as diseases affecting metabolism such as lysosomal diseases and in particular the disease MPS VII or Sly syndrome.

The present invention also relates to a pharmaceutical composition comprising one or more recombinant baculoviruses as described above. These pharmaceutical compositions may be formulated for administration by various routes and in particular by the intramuscular, subcutaneous, intraocular, transdermal, intracerebral, intraventricular or intramedullary route and the like. Preferably, the pharmaceutical compositions of the invention contain a pharmaceutically acceptable vehicle for an injectable formulation, especially for a direct injection into the nervous system of the patient. They may be in particular isotonic sterile solutions or dry, especially freeze-dried, compositions which, upon addition, depending on the case, of sterilized water or physiological saline, allow the constitution of injectable solutions. Direct injection into the nervous system of the patient is advantageous because it makes it possible to concentrate the therapeutic effect at the level of the affected tissues. Direct injection into the central nervous system of the patient is advantageously carried out by means of an apparatus for stereotaxic injection. The use of such an apparatus indeed makes it possible to target the site of injection with great precision.

In this regard, the invention also relates to a method of treating diseases of the nervous system, such as for example neurodegenerative or metabolic diseases, comprising the administration, to a patient, of a recombinant baculovirus as defined above. More particularly, the invention relates to a method of treating neurodegenerative and/or lysosomal diseases comprising the stereotaxic administration of a recombinant baculovirus as defined above.

The doses of virus used for the injection may be adjusted according to various parameters, and in particular according to the mode of administration used, the relevant pathology, the gene to be expressed or alternatively the desired duration of treatment. In general, the recombinant baculoviruses according to the invention are formulated and administered in the form of doses of between $10^4$ and $10^{14}$ pfu/ml, and preferably $10^6$ to $10^{10}$ pfu/ml. The term pfu (plaque forming unit) corresponds to the infectivity of a viral solution and is determined by infecting an insect cell culture and measuring, generally after 5 days, the number of plaques of infected cells or else by titration by limiting dilution. The techniques for determining the pfu titer of a viral solution are well documented in the literature.

Another subject of the invention relates to any mammalian cell infected by one or more recombinant baculoviruses as described above. More particularly, the invention relates to any human nerve cell population infected by these baculoviruses. This may be in particular glial (astrocyte, microglial, oligodendrocyte, Schwann cell), ependymal or neural cells and the like.

The cells according to the invention may be derived from primary cultures. These may be collected by any technique known to persons skilled in the art and then cultured under conditions allowing their proliferation. As regards more particularly autologous transplants, they may be astrocytic cells, preferably adult human astrocytic cells. As regards heterologous transplants, they may be embryonic cells, preferably human embryonic cells, nerve or neuronal progenitor cells such as the progenitors derived from human telencephalon or mesencephalon which may be possibly differentiated in vitro before transplant, embryonic astrocytes; it being possible for these cells to be obtained easily from biopsies. They may also be xenotransplants derived from pheochromocytomas, or embryonic cells or astrocytes or other types of cells such as Sertoli cells. The cells may also be ES cells (Embryonic Stem cells), preferably human ES cells, differentiated in a nervous pathway for example. These cells may be used directly for infection with the baculoviruses or stored, for example by freezing, for the establishment of autologous libraries for a subsequent use. The cells according to the invention may also be secondary cultures obtained for example from preestablished libraries.

The cells in culture are then infected with recombinant baculoviruses so as to confer on them the capacity to produce a substance of therapeutic interest. The infection is carried out in vitro according to techniques known to persons skilled in the art. In particular, according to the type of cells used and the number of copies of virus per cell desired, persons skilled in the art can adjust the multiplicity of infection and optionally the number of cycles of infection performed. It is clearly understood that these steps should be carried out under appropriate sterile conditions when the cells are intended for administration in vivo. The doses of recombinant baculovirus used for the infection of the cells may be adjusted by persons skilled in the art according to the desired aim. The conditions described above for the administration in vivo can be applied to infection in vitro.

Another subject of the invention relates to an implant comprising human cells infected with one or more recombinant baculoviruses as described above, and an extracellular matrix. Preferably, the implants according to the invention comprise $10^4$ to $10^{10}$ cells. More preferably, they comprise $10^6$ to $10^8$ cells.

More particularly, in the implants of the invention, the extracellular matrix comprises a gelling compound and optionally a support allowing anchorage of the cells.

For the preparation of the implants according to the invention, the various types of gelling agents may be used. The gelling agents are used for the inclusion of the cells in a matrix having the constitution of a gel and to promote anchorage of the cells on the support, where appropriate. Various cell adhesion agents can therefore be used as gelling agents, such as in particular collagen, gelatin, glycosaminoglycans, fibronectin, lectins and the like. Preferably, collagen is used in the context of the present invention. This may be collagen of human, bovine or murine origin. More preferably, type I collagen is used.

As indicated above, the compositions according to the invention advantageously comprise a support allowing anchorage of the cells. The term anchorage designates any form of biological and/or chemical and/or physical interaction bringing about the adhesion and/or attachment of the cells onto the support. Moreover, the cells may either cover the support used, or penetrate inside this support, or both. The use of a nontoxic and/or biocompatible solid support is preferred in the context of the invention. In particular, polytetrafluoroethylene (PTFE) fibers or a support of biological origin may be used.

The implants according to the invention may be implanted at various sites in the body. In particular, the implantation may be carried out in a muscle, a tumor, the central nervous system or alternatively under a mucous membrane. The implants according to the invention are particularly advantageous in the sense that they make it possible to control the release of the therapeutic product in the body: this is first of all determined by the multiplicity of infection and by the number of implanted cells. Next, the release may be controlled either by withdrawing the implant, which stops the treatment permanently, or by the use of regulatable expression systems which make it possible to induce or to repress the expression of the therapeutic genes.

The present invention thus offers a very effective means for the treatment or prevention of diseases of the nervous system. It is most particularly suitable for the treatment of Alzheimer's disease, Parkinson's disease, Huntington's disease and ALS, or alternatively lysosomal diseases. The baculoviruses according to the present invention have, in addition, considerable advantages linked in particular to their low immunogenicity, because of the lack of expression of the baculovirus proteins in mammalian cells.

The present invention will be described in greater detail with the aid of the following examples which should be considered as illustrative and nonlimiting.

Materials and Methods

General Molecular Biology Techniques

The methods conventionally used in molecular biology, such as preparative extractions of plasmid DNA, centrifugation of plasmid DNA in cesium chloride gradient, agarose or acrylamide gel electrophoresis, purification of DNA fragments by electroelution, extraction of proteins with phenol or phenol-chloroform, ethanol or isopropanol precipitation of DNA in saline medium, transformation in *Escherichia coli* and the like, are well known to persons skilled in the art and are widely described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York, 1987].

For the ligations, the DNA fragments can be separated according to their size by agarose or acrylamide gel electrophoresis, extracted with phenol or with phenol/chloroform mixture, precipitated with ethanol and then incubated in the presence of phage T4 DNA ligase (Biolabs) according to the recommendations of the supplier.

The filling of the protruding 5' ends can be performed with Klenow fragment of *E. coli* DNA polymerase I (Biolabs) according to the specifications of the supplier. The destruction of the protruding 3' ends is performed in the presence of phage T4 DNA polymerase (Biolabs) used according to the recommendations of the manufacturer. The destruction of the protruding 5' ends is performed by a controlled treatment with S1 nuclease.

Site-directed mutagenesis in vitro by synthetic oligodeoxynucleotides can be performed according to the method developed by Taylor et al. [Nucleic Acids Res. 13 (1985) 8749–8764] using the kit distributed by Amersham.

The enzymatic amplification of DNA fragments by the so-called PCR technique [Polymerase-catalyzed Chain Reaction, Saiki R. K. et al., Science 230 (1985) 1350–1354; Mullis K. B. and Faloona F. A., Meth. Enzym. 155 (1987) 335–350] can be performed using a DNA thermal cycler (Perkin Elmer Cetus) according to the specifications of the manufacturer.

The verification of the nucleotide sequences can be performed by the method developed by Sanger et al. [Proc. Natl. Acad. Sci. USA, 74 (1977) 5463–5467] using the kit distributed by Amersham.

LEGEND TO THE FIGURES

FIG. 1: Percentage of GFP-positive cells preserved in the undifferentiated state by addition of bFGF to the medium, as a function of the quantity of baculovirus Bac-CMV-GFP (1 µl corresponding to an MOI of 5).

Figure 2:
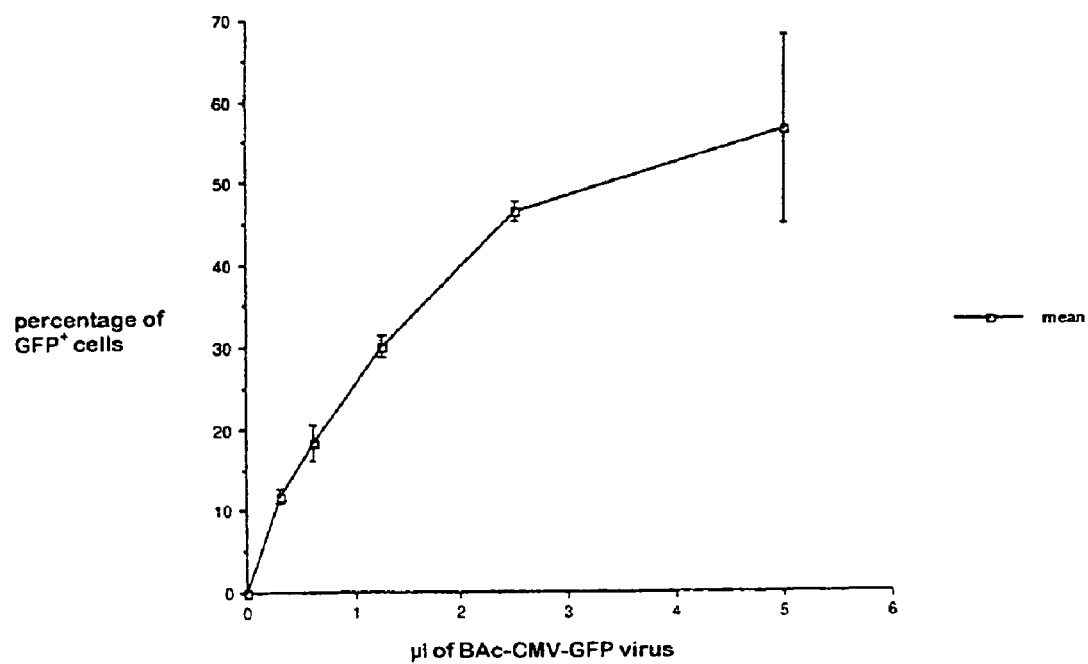

FIG. 2: Percentage of GFP-positive cells cultured in the presence of 10% of serum (differentiated state), as a function of the quantity of baculovirus Bac-CMV-GFP (1 µl corresponding to an MOI of 5).

Figure 3:
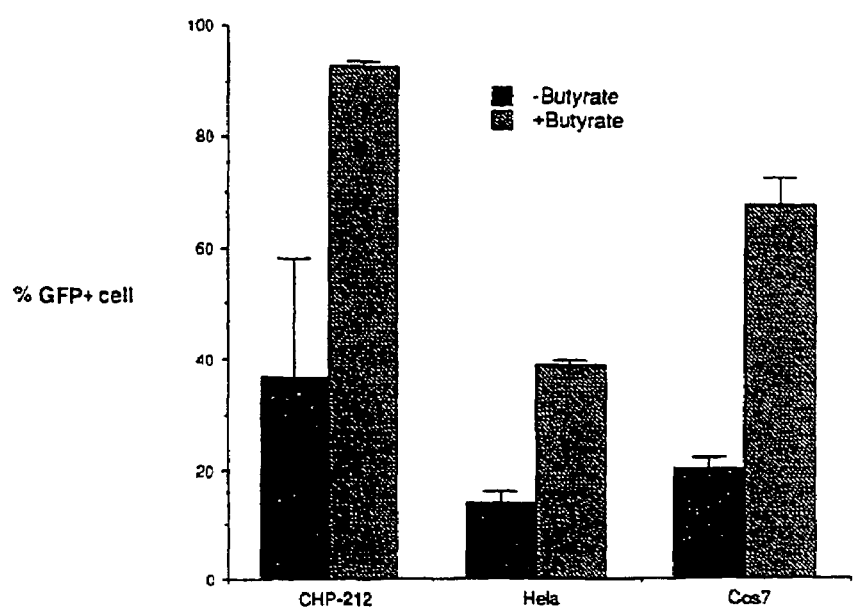

FIG. 3: Comparison and demonstration of the action of butyrate in several cell lines: CHP-212, Hela, Cos 7. The infection and expression is very significant in particular in the CHP-212 cells. The addition of butyrate allows expression of GFP in pratically 100% of these cells.

Figure 4:
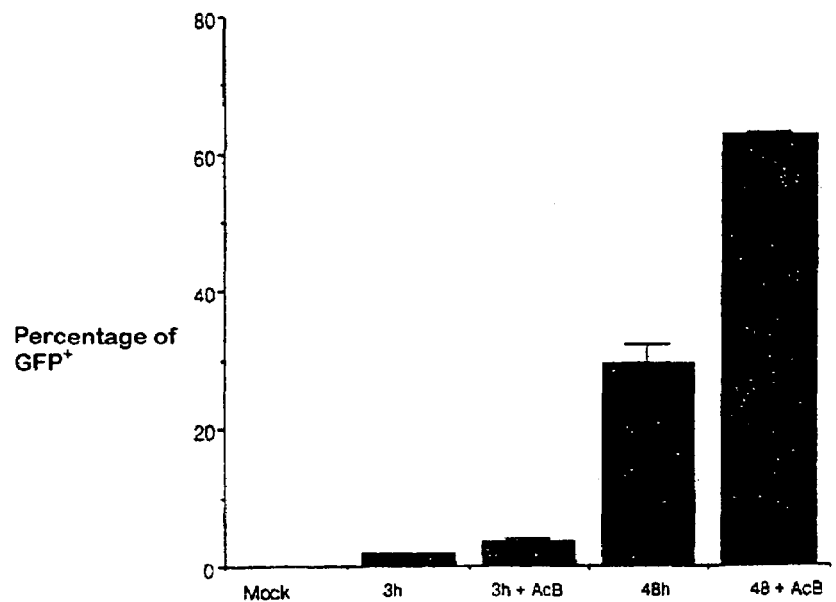

FIG. 4: Demonstration of the action of butyrate on the infection of progenitor cells cultured in the presence of 10% of FCS 48 hours after infection:

4A: action of butyrate expressed as a percentage of GFP-positive cells. 48 hours after infection, more than 60% of the cells express GFP.

4B: action of butyrate expressed as fluorescence intensity. 48 hours after infection, the fluoroescence intensity is much higher in the cells subjected to the action of butyrate (intensity of about 425 with butyrate versus an intensity equal to 100 without butyrate).

Figure 5A:
Figure 5B:
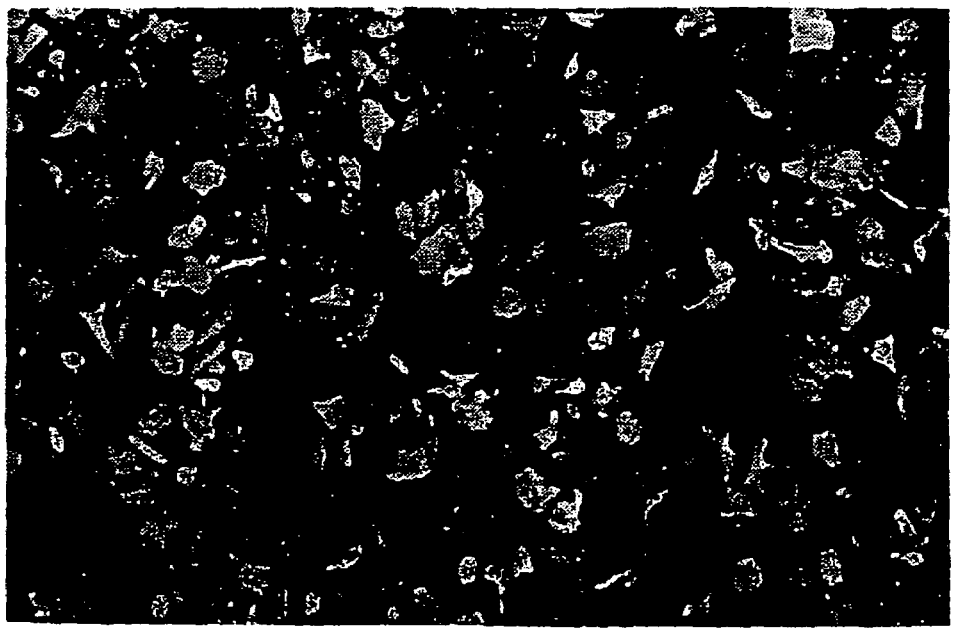

FIG. 5: Results of the in vitro expression of GFP after infection by Bac-CMV-GFP of a culture of human embryonic telencephalic cells:

5A: culture of human embryonic telencephalic cells with 10% of FCS. The great majority of these cells are astrocytes.

5B: culture of human embryonic telencephalic cells with 10% of FCS and butyrate. All the cells express GFP.

Figure 6A:
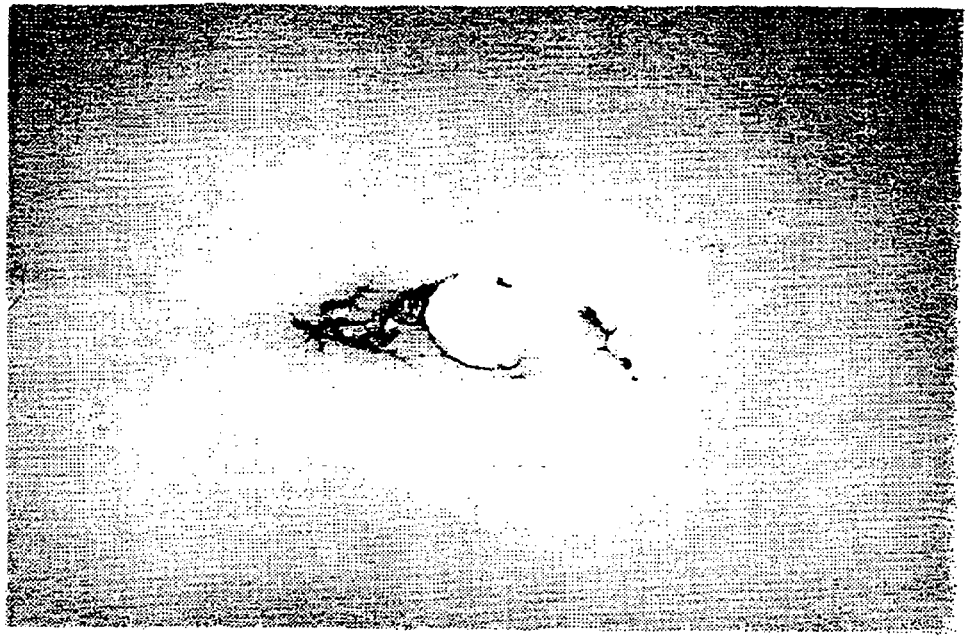
Figure 6B:
Figure 6C:

FIG. 6: Results of the expression of GFP in vivo one week after stereotaxic injection in Balb C mice of the baculovirus bac-CMV-GFP:

6A: expression of GFP in the striatum. Morphologically, the labelled cells appear to be blood vessel epithelial cells as well as a few nerve cells (astrocytes) surrounding the blood vessel.

6B: expression of GFP in the striatum. The labelled cells are astrocytes.

6C: expression of GFP in the lateral ventricle. The labelled cells are ependymal cells.

Figure 7:
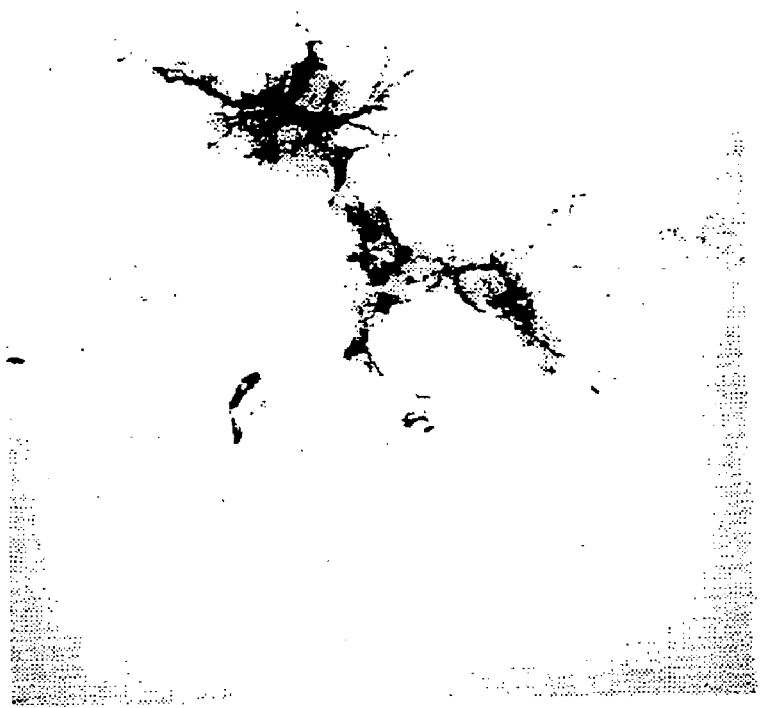

FIG. 7: Results in the striatum of the expression of GFP in vivo 48 hours after stereotaxic injection in rats, of the baculdvirus bac-CMV-GFP. The injection was carried out under the same conditions as described in Example 4 (9 µl of virus diluted 1:10). The GFP-expression labelling was carried out by means of an anti-GFP antibody (Clontech).

EXAMPLES

Example 1

Construction of Various Baculovirus Vectors 1.1—Construction and Production of the Baculovirus RSV-LacZ;

The recombinant baculovirus RSV-LacZ was obtained by homologous recombination between a shuttle plasmid and the genome of *Autographa california* in SF9 cells and amplified in these same cells according to the method described by Gruenwald S. and Heitz J., 1993 (Baculovirus expression vector system, procedure & method manual. Pharmingen Eds, San Diego, Calif.).

The shuttle plasmid was produced by inserting into the plasmid pVL1392 (Pharmingen, San Diego, Calif.) an expression cassette for the nuclear beta-galactosidase gene under the control of the RSV LTR, and the SV40 polyadenylation signal downstream of the LacZ gene. This expression cassette was inserted into the multiple cloning site in the reverse orientation in relation to the polyhedrin promoter contained in the plasmid pVL1392.

The virus is then produced by amplification in Sf9 cells. It is concentrated by ultracentrifugation of 180 ml of supernatant (titer initially determined at $3\times10^7$ pfu/ml at 25,000 rpm at 4° C. for 90 minutes in an SW 28 rotor and then taken up in 2 ml of PBS and ultracentrifuged at 25,000 rpm at 4° C. for 90 minutes in an SW 41 rotor in a sucrose gradient (10% to 60%, in PBS). The white band corresponding to the purified viral particles is collected and resuspended in PBS and ultracentrifuged at 25,000 rpm at 4° C. for 90 minutes. The pellet is resuspended in 1.5 ml of cold PBS. This concentrated and purified virus stock is stored at 4° C. or at −80° C.

1.2—Construction and Production of the Baculovirus CAG-LacZ:

The recombinant baculovirus CAG-LacZ was obtained using the shuttle plasmid pAcYM1 (Matsuura et al, J. of Gen. Virol. 68 (1987) 1233–1250). An expression cassette containing the CAG promoter controlling the expression of the LacZ gene was inserted into the shuttle plasmid. The CAG promoter is a composite promoter consisting of a CMV IE enhancer, the promoter of chicken beta-actin and the polyadenylation signal of rabbit beta-globin.

The recombinant baculovirus was obtained by homologous recombination in Sf9 cells and then amplified in these cells (according to the protocol of Matsuura et al., J. of Gen. Virol. 68 (1987) 1233–1250).

The virus used was obtained by amplification of an aliquot of the recombinant baculovirus in Sf9 cells. The titer of the viral solution was determined at $1\times10^9$ pfu/ml. The virus is then concentrated by a factor of 100 and purified under the same conditions as those described for the baculovirus RSV-LacZ.

1.3 Construction and Production of the Baculovirus CMV-GFP

The aim of this example is to describe the construction of a recombinant baculovirus carrying a very active expression cassette cloned from the vector pCI vector (Promega) and containing the gene for the Green Fluorescent Protein (EGFP), cloned from the EGFP plasmid (Clontech), under the control of a CMV promoter and a chimeric intron (comprising the 5' splicing site of the β-globin intron and the 3' splicing site of an IgG intron for example) placed upstream of the transgene and an SV40 polyA.

First of all, a shuttle plasmid Bac-CMV containing an expression cassette comprising the CMV early promoter, the SV40 late polyadenylation signal and a multiple cloning site was constructed in order to be able to clone any cDNA for the expression of the latter in mammalian cells. Initially, the cassette was cloned into a vector pVL1392 (Invitrogene), in the reverse orientation to the polyhedrin promoter in order to prevent any transcriptional interference with the baculovirus polyhedrin promoter. The GFP reporter gene was cloned into the shuttle plasmid (Bac-CMV) in order to produce the plasmid Bac-CMV-GFP.

This shuttle plasmid was then transfected into Sf9 insect cells for the production of recombinant baculoviruses, by homologous recombination with the linearized genome of *Autographa california* (AcNPV). When the virus was amplified on Sf9 insect cells, it was possible for the expression of GFP to be detected by fluorescence microscopy, thus demonstrating that the CMV promoter was active in these cells.

After amplification, the viral stock (Bac. CMV-GFP) was successively concentrated and purified according to the methods previously described. The aliquots were stored at −80° C.

Example 2

Test of Infection In Vitro of Various Cell Cultures by the Baculovirus RSV-Lacz 2.1—Infection of Primary Cultures of Adult Astrocytes:

The cells are cultured in four-well plates. The infection is made at 37° C. in serum-free culture medium for about 2 h. It is made with increasing concentrations of recombinant virus. After 24 h, the cells are fixed (4% PFA) and stained with X-Gal. The noninfected controls do not have any blue cell.

Observation of the cultures at 24 and 48 hours after the infection shows that the recombinant baculovirus is capable of infecting cells of a primary culture of human astrocytes (human telencephalon cultured in bFGF) and of expressing the LacZ gene (observed by X-Gal reaction).

2.2—Infection of Primary Cultures of Human Embryonic telencephalon:

The cells are cultured in a medium containing bFGF (medium which makes it possible to maintain them in a state of undifferentiated or only very slightly differentiated progenitor cells). The infection was made in complete culture medium for 2 h. The noninfected controls have no blue cells.

Observation of the cultures four days after the infection shows that the recombinant baculovirus is capable of infecting human progenitor nerve cells (human telecephalon cultured in bFGF) and of expressing the LacZ gene (observed by X-Gal reaction).

All these results demonstrate that the recombinant vectors derived from baculoviruses are capable of infecting various types of primary cultures of neural cells in vitro and can thus be used as vector for gene therapy for the transfer of genes ex vivo.

Example 3

Test of In Vitro Infection of Various Cell Cultures with the Baculovirus Bac-CMV-GFP 3.1 Infection of Various Cell Lines In order to assess the efficacy of the vector Bac-CMV-GFP for gene transfer into mammalian cells, the potential activity of this vector to infect and to direct the expression of the GFP reporter gene in various neuronal (CHP212) and normeuronal (HuH7, 293, HeLa, Cos7) lines was studied. For that, the cell lines HuH7 (human hepatocytes), 293 (human kidneys), HeLa (human epithelium), Cos7 (monkey kidney), N2A (murine neuroblastoma cells) and CHP212 (human neuroblastoma cells) were infected with this vector at an MOI of 12.5. At this vector concentration, the analysis of the fluorescent cells by flow cytometry makes it possible to observe that nearly 100% of the HuH7 and 293 cells are transduced, as well as a high proportion of the CHP212 cells and, to a lesser extent, of the HeLa, Cos7 and N2A cells (of the order of 5 to 20%).

In order to document the phenomena of transcriptional repression of these vectors, the transduced cells were treated with a histone deacetylase inhibitor (butyrate). Indeed, this agent is described as a potent factor capable of lifting the inhibitions of transcription which are due to the condensation of chromatin. Thus, in each case, it was possible to show a significant increase in the number of cells expressing the transgene. Likewise, a high increase in the quantity of flurorescence by cells after induction with butyrate was recorded.

These experiments show the capacity of this vector to effectively transduce a wide range of mammalian cells. Indeed, it was observed that this vector makes it possible to very effectively transduce a human neuronal line (CHP212).

3.2 Infection of Primary Cultures of Nerve Cells in Vitro

In the same manner as for the cell lines, the vector Bac-CMV-GFP was used to transduce human or rodent primary nerve cells.

Initially, human primary neuroepithelial progenitor cells were infected and cultured in a medium containing bFGF (progenitor state) or cultured in the presence of serum (cells differentiated predominantly in the glial system) with an increasing range of vector up to a quantity corresponding to an MOI of 25. Two days after the infection, analysis by flow cytometry reveals the presence of the order of 30% of progenitor cells-bFGF and of the order of 60% of differentiated progenitor cells, expressing GFP as shown by FIGS. 1 and 2 respectively. It is of interest to note that the dose/response curve in the case of the progenitor cells did not reach a plateau at an MOI of 25, suggesting that these cells may be infected more substantially.

Moreover, double-labelling experiments in vitro on human cells of the embryonic telencephalon with the aid of the markers GFAP (astrocyte marker) and MAP 5 (neuron markers) clearly show that these two types of cell are infectable. Indeed, the results provide a GFAP/GFP and MAP5/GFP labelling demonstrating unexpectedly that not only the astrocytes but also the neurons are infected.

Figure 4B:
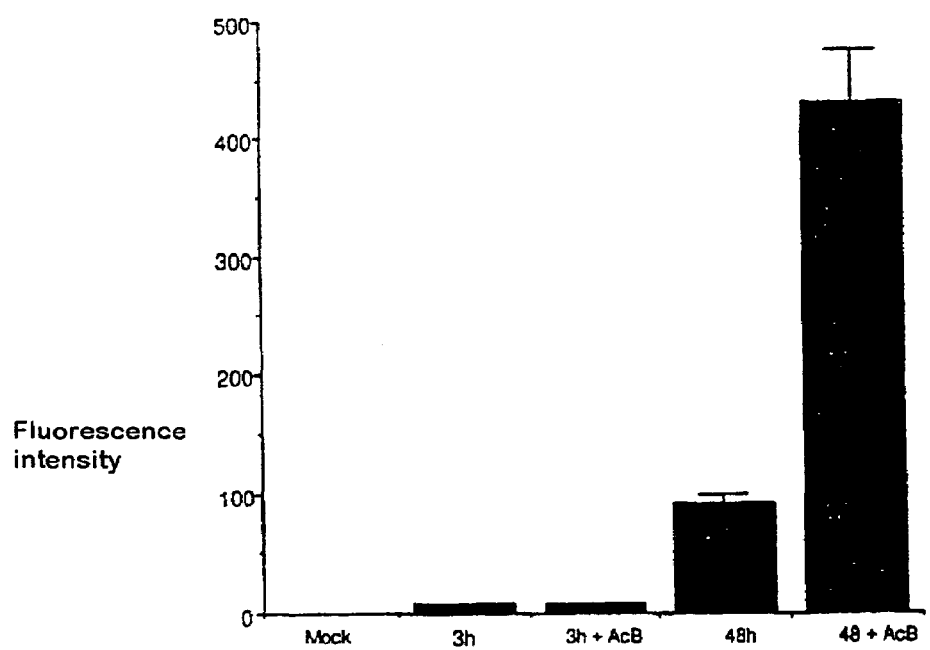

In parallel, it was checked on the same cells that the level of "pseudotransduction", that is to say that the number of GFP+cells which did not synthesize de novo novel [lacuna] of the reporter gene was in all cases less than 3% of the GFP-positive cells. For that, the presence of fluorescence was tested for three hours after the infection, a duration which does not allow effective expression of GFP according to the mechanism of transcription and translation of the GFP gene (FIGS. 4A and 4B). Furthermore, the inactivation of the viruses by UV irradiation (with a UV-crosslinker at a dose of 100 000 μjoules approximately) before the infection made it possible to show that there was no longer practically any (less than 3%) GFP-positive cells, therefore confirming the results obtained in pseudotransduction.

The effect of the butyrate was also evaluated on glial cells obtained by differentiation of cultures of human nerve progenitors infected with Bac-CMV-GFP. Twenty-four hours after supplementation of the inducer in the culture medium, a doubling of the number of GFP-positive cells relative to the untreated cells was observed. The mean fluorescence value in the treated cells was however about four times higher than that observed in the untreated cells. These data strongly suggest an epigenetic mechanism of transcriptional repression in the same manner as previously described for the cell lines. These results show, in addition, that the vector of the invention makes it possible to infect adult human primary astrocytes as well as rat primary pinealocytes.

This example therefore demonstrates that a baculovirus containing an expression cassette comprising a promoter (CMV) and a heterologous gene (GFP) is capable of infecting normeuronal cells but also surprisingly neuronal cells (CHP212 line) as well as nerve cells derived from primary cultures (embryonic or adult) and of directing the expression of the heterologous gene in the said cells at a very significant level.

Example 4

Test In Vivo with the Baculovirus RSV-Lacz 4.1—Stereotaxic Injection into Rat Striatum:

Sprague-Dowley adult female rats were injected with 9 μl of concentrated RSV-LacZ virus. The injection was made by slow injection of 1 μl of virus (0.25 μl/min) at three sites of injection with 3 subsites for each of the sites.

Stereotaxic coordinates relative to the Bregma:

A: +1.8, L: +2.5, V0: −5, V1: −4.6, V2: −4.2
A: +0.6, L: +3.2, V0: −5, V1: −4.6, V2: −4.2
A: +0.6, L: +2, V0: −5, V1: −4.6, V2: −4.2

5 days after infection, the rats are fixed by intracardial infusion of 4% PFA in PBS and the brains post-fixed for 24 h at 4° C. in 4% PFA. The brains are then cryoprotected by immersing in 15% sucrose in PBS for 72 h. The brains are then frozen in cold isopentane (−50° C.) and then preserved at −80° C.

4.2—Histology on the Brains of the Rats Injected:

The brains are cut at the level of the striatum with a cryostat (section thickness: 20 μm). The sections are studied by immunohistochemistry in order to detect the presence of $E\ coli$β-galactosidase. The slides are washed in PBS, incubated in methanol+0.3% $H_2O_2$ for 1 hour, washed in PBS and then preincubated for 2 h with PBS+10% FCS+0.1% Triton. Next, they are incubated overnight with the anti-1-Gal antibody (Cappel: 1:5000th), washed with PBS and then incubated with the secondary antibody (Vectastain Goat Anti-Rabbit Kit). The visualization is carried out in DAB+Nickel. Thus, a large number of labelled cells was observed in the two brains (on about 100 sections, making a thickness of about 2 mm around the injection site).

A double fluorescent labelling β-Gal+GFAP was carried out using an anti-β-Gal monoclonal antibody (Promega) and an anti-GFAP polyclonal antibody. Very few cells are doubly labelled.

Transduction and a more pronounced labelling of the cells at the periphery of the callous body as well as of the cells in the striatum are observed.

The study, by immunohistochemistry, with the anti-βgal antibody demonstrates that the recombinant baculovirus allows the infection and expression of the transgene in a large number of nerve cells. It also shows that the recombinant baculovirus is not activated by complement in the CNS.

Example 5

In Vivo Test with the Baculovirus Bac-CMV-GFP

The aim of this example is to demonstrate the capacity of the vector Bac-CMV-GFP to infect nerve cells in vivo.

The vector Bac-CMV-GFP at $10^6$ pfu was injected into the striatum of adult Sprague Dawley rats and of adult Nude or Balb-C mice. The stereotaxic coordinates for injection are the following:

For the rats (Sprague Dawley adult female, 200–250 g): injection of 9 μl at the rate of 0.25 μl per minute in the case of injection of dilute virus, carried out according to the same conditions as in Example 4. An injection of 2 μl at the rate of 0.125 μl/minute may also be carried out.

Stereotaxic coordinates relative to the Bregma:
A: +1, V: +2.3, L: −5,

For the mice (Nude or Balb-C adult female, 20–25 g): injection of 2 μl at the rate of 0.1 μl per minute.

Stereotaxic coordinates relative to the Lambda:
A: +4.7, L: +1.7, V: −3.6,

At two days and one week postinjection, the presence of striatal cells expressing GFP was detected in the two species. In addition to the striatum, other cells expressing GFP were also detected in the corpus callosum and in the ependyma (FIGS. 6A, 6B, 6C and FIG. 7).

Immunohistochemical phenotyping makes it possible to demonstrate a very high majority of GFP/GFAP-positive cells, suggesting a very preferentially glial tropism of this vector in the brain.

These results therefore demonstrate in an obvious manner the capacity of the baculovirus to infect neural cells in vivo.

What is claimed is:

1. A method for expressing a polypeptide preferentially in glial cells of the central nervous system, the method comprising administering stereotaxically into the central nervous system of a subject a recombinant baculovirus, said baculovirus having a baculovirus envelope protein and comprising a heterologous nucleic acid sequence encoding the polypeptide operatively associated with a CMV (cytomegalovirus) promoter, thereby causing expression of the polypeptide preferentially in glial cells.

2. The method according to claim 1, wherein the heterologous nucleic acid sequence encodes a product of therapeutic interest which is operatively associated with CMV (cytomegalovirus) promoter, and the product of therapeutic interest is mainly expressed in glial cells.

3. The method according to claim 1, wherein the heterologous nucleic acid sequence is a gene that encodes a compound selected from the group consisting of a hormone, a lymphokine, a growth factor, an enzyme for synthesizing a neurotransmitter, a trophic factor, a protein involved in the metabolism of an amino acid, a protein involved in the metabolism of a lipid, and a protein involved in the metabolism of a carbohydrate.

4. The method according to claim 3, wherein trophic factor is selected from the group consisting of a neurotrophin, a member of the CNTF (Ciliary NeuroTrophic Factor) family, a member of the IGF (Insulin Like Growth Factor) family, and a member of the FGF (Fibroblast Growth Factor) family.

5. The method according to claim 3, wherein the heterologous nucleic acid sequence encodes β-glucuronidase.

6. The method according to claim 4, wherein the neurotrophin is selected from the group consisting of NGF (Nerve Growth Factor). BDNF (Brain-Derived Neurotrophic Factor), NT3 (Neurotrophin-3), NT4/5 (Neurotrophin-4/5), and NT6 (Neurotrophin-6); the member of the CNTF family is selected from the group consisting of CNFT (Ciliary NeuroTrophic Factor), axokine, LIF (Leukemia Inhibitory Factor), IL6 (InterLeukin-6), cardiotrophin, and GDNF (Glial cell line-Derived Neurotrophic Factor); the member of the IGF family is selected from the group consisting of IGF-1 and IFGF-2; and the member of the FGF family is selected from the group consisting of FGF1, FGF2, FGF3, FGF4, FGF5, FGF6, FGF7, FGF8, FGF9, and TFG-β (Transforming Growth Factor-β).

* * * * *